United States Patent
Heo et al.

(10) Patent No.: US 11,963,791 B2
(45) Date of Patent: Apr. 23, 2024

(54) TRAINING SYSTEMS AND METHODS FOR PREDICTING KNEE ADDUCTION MOMENT

(71) Applicant: UNIVERSITY OF MARYLAND, COLLEGE PARK, College Park, MD (US)

(72) Inventors: Yunjung Heo, Yongin-si (KR); Jumyung Um, Yongin-si (KR); Jae Kun Shim, Clarksville, MD (US); Samantha Snyder, Columbia, MD (US); Ross Miller, Cabin John, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 18/274,049

(22) PCT Filed: Jan. 25, 2022

(86) PCT No.: PCT/US2022/013712
§ 371 (c)(1),
(2) Date: Jul. 25, 2023

(87) PCT Pub. No.: WO2022/159893
PCT Pub. Date: Jul. 28, 2022

(65) Prior Publication Data
US 2024/0041394 A1 Feb. 8, 2024

Related U.S. Application Data

(60) Provisional application No. 63/141,429, filed on Jan. 25, 2021, provisional application No. 63/166,223, (Continued)

(51) Int. Cl.
*A61B 5/00* (2006.01)
*A61B 5/11* (2006.01)
*G06T 7/00* (2017.01)

(52) U.S. Cl.
CPC ........ *A61B 5/4585* (2013.01); *A61B 5/1127* (2013.01); *G06T 7/0012* (2013.01);
(Continued)

(58) Field of Classification Search
None
See application file for complete search history.

(56) References Cited

U.S. PATENT DOCUMENTS

2016/0367199 A1* 12/2016 Stefanyshyn ........ A61B 5/1038
2017/0042467 A1* 2/2017 Herr ...................... A61B 5/112
(Continued)

OTHER PUBLICATIONS

Stetter, Bernd J., et al. "A machine learning and wearable sensor based approach to estimate external knee flexion and adduction moments during various locomotion tasks." Frontiers in bioengineering and biotechnology 8 (2020): 9. (Year: 2020).*
(Continued)

*Primary Examiner* — Samah A Beg
(74) *Attorney, Agent, or Firm* — George Likourezos; Carter, DeLuca & Farrell LLP (57) ABSTRACT

A method for training an algorithm for predicting a knee adduction moment (KAM) includes, while each subject walks over forceplates, capturing kinematic data, generating first ground reaction force (GRF) data, generating second GRF data, and generating reference KAM data based on the kinematic data and the first GRF data. While repeatedly training the algorithm by incrementing i by one, the method performs generating a model, which predicts reference KAM data, validating the predicted reference KAM data based on reference KAM data of the subjects other than the i-th subject, adjusting internal parameters by minimizing an error between the predicted KAM data and reference KAM data of the subjects other than the i-th subject, and producing an accuracy score for the model based on an error between
(Continued)

the predicted reference KAM data and the reference KAM data of the i-th subject.

20 Claims, 9 Drawing Sheets

Related U.S. Application Data filed on Mar. 25, 2021, provisional application No. 63/267,097, filed on Jan. 24, 2022.

(52) U.S. Cl.
CPC ............... *G06T 2207/20081* (2013.01); *G06T 2207/20084* (2013.01)

(56) References Cited

U.S. PATENT DOCUMENTS

2018/0235830 A1* 8/2018 Rokosz ..................... A61H 3/00
2020/0397384 A1* 12/2020 Cheung ................ A61B 5/7264

OTHER PUBLICATIONS

Wang, Chao, et al. "Real-time estimation of knee adduction moment for gait retraining in patients with knee osteoarthritis." IEEE Transactions on Neural Systems and Rehabilitation Engineering 28.4 (2020): 888-894. (Year: 2020).*

International Search Report and Written Opinion issued in corresponding International Application No. PCT/US2022/013712, dated May 11, 2022, pp. 1-9.

International Preliminary Report on Patentability issued by the International Bureau of WIPO in connection with International Application No. PCT/US2022/013712, dated Jul. 20, 2023.

M.A. Boswell, et al., "Osteoarthritis and Cartilage", OARSI Osteoarthritis, pp. 1-10, Jan. 21, 2021.

Asma Channa, et al., "Design and Application of a Smart Diagnostic System for Parkinson's Patients using Machine Learning", International Journal of Advanced Computer Science and Applications, vol. 10, No. 6, pp. 1-9, Jun. 2019.

Ahnryul Choi, et al., "Machine learning approach to predict center of pressure trajectories in a complete gait cycle: a feedforward neural network vs. LSTM network", Medical & Biological Engineering & Computing, pp. 1-11, Nov. 14, 2019.

Stephanie Eng, et al., "A 6 DoF, Wearable, Compliant Shoe Sensor for Total Ground Reaction Measurement", IEEE Transactions of Instrumentation and Measurement, pp. 1-9, 2018.

Julien Favre, et al., "A neural network model to predict knee adduction moment during waling based on ground reaction force and anthropometric measurements", Journal of Biomechanics, pp. 1-7, Nov. 27, 2011.

Daniel Tik-Pui Fong, et al., "A three-pressure-sensor (3PS) system for monitoring ankle supination torque during sport motions", Journal of Biomechanics 41, pp. 1-5, May 28, 2008.

Daniel Tik-Pui-Fong, et al., "Estimating the complete ground reaction forces with pressure insoles in walking", Journal of Biomechanics, pp. 1-5, May 9, 2008.

A. Forner Cordero, et al., "Use of pressure insoles to calculate the complete ground reaction forces", Journal of Biomechanics, pp. 1-6, Dec. 18, 2003.

Zexia He, et al., "A Wearable Sensing and Training System: Towards Gait Rehabilitation for Elderly Patients With Knee Osteoarthiitis", IEEE Sensors Journal, vol. 19, No. 14, pp. 1-10, Jul. 15, 2019.

Nagaraj Hegde, et al., "Automatic Recognition of Activities of Daily Living utilizing Insole Based and Wrist Worn Wearable Sensors", IEEE Journal of Biomedical and Health Information, pp. 1-9, 2017.

Adam M. Howell, et al., "A Laboratory Insole for Analysis of Sensor Placement to Determine Ground Reaction Force and Ankle Moment in Patients with Stroke", 34th Annual International Conference of the IEEE EMBS, pp. 1-4, 2012.

Daniel A. Jacobs, et al., "Estimation of ground reaction forces and ankle moment with multiple, low-cost sensors", Journal of Neuroengineering and Rehabilitation, pp. 1-12, 2015.

Gu-Min Jeong, et al., "Classification of Three Types of Walking Activities Regarding Stairs Using Plantar Pressure Sensors", IEEE Sensors Journal Letters, pp. 1-2, Jan. 2017.

Su-Bin Joo, et al., "Improving the ground reaction force prediction accuracy using one-axis plantar pressure: Expansion of input variable for neural network", Journal of Biomechanics, pp. 1-9, 2016.

Jason M. Konrath, et al., "Estimation of the Knee Adduction Moment and Joint Contact Force during Daily Living Activities Using Inertial Motion Capture", Sensors, pp. 1-12, Apr. 9, 2019.

Virginia Byers Kraus, et al., "Call for Standardized Definitions of Osteoarthritis and Risk Stratification for Clinical Trials and Clinical Use", HHS Public Access, Osteoarthritis Cartilage, pp. 1-19, Aug. 1, 2016.

Tao Liu, et al., "New Method for Assessment of Gait Variability Based on Wearable Ground Reaction Force Sensor", 30th Annual International IEEE EMBS Conference, pp. 1-4, Aug. 2008.

Nhan Duc Nguyen, et al., "Classification of Five Ambulatory Activities Regarding Stair and Incline Waling Using Smart Shoes", IEEE Sensors Journal, pp. 1-7, Mar. 2018.

Fang Pu, et al., "Optimal Estimation of Total Plantar Force for Monitoring Gait in Daily Life Activities with Low-Price Insole System", Journal of Mechanics in Medicine and Biology, pp. 1-16, Jan. 23, 2014.

H. Rouhani, et al., "Ambulatory assessment of 3D ground reaction force using plantar pressure distribution", Gait and Posture, 32(3), pp. 1-6, 2010.

H. Rouhani, et al., "A wearable system for multisegment foot kinetics measurement", Journal of Biomechanics, 47(7), pp. 1-8, 2014.

H.H.C.M. Savelberg, et al., "Assessment of the horizontal, fore-aft component of the ground reaction force from insole pressure patterns by using artificial neural networks", Clinical Biomechanics, 14(8), pp. 1-8, 1999.

Taeyong Sim, et al., "Predicting Complete Ground Reaction Forces and Moments During Gait With Insole Plantar Pressure Information Using a Wavelet Neural Network", Journal of Biomechanical Engineering, 137(9), pp. 1-9, 2015.

S. Sivakumar, et al., "Artificial neural network based ankle joint angle estimation using instrumented foot insoles", Biomedical Signal Processing and Control, 54, 101614, pp. 1-9, 2019.

B. Stetter, et al., "Machine Learning and Wearable Sensor Based Approach to Estimate External Knee Flexion and Adduction Moments During Various Locomotion Tasks", Frontiers in Bioengineering and Biotechnology, 8, 9, pp. 1-11, Jan. 2020.

H. Zhang, et al., "Regression Models for Estimating Kinematic Gait Parameters with Instrumented Footwear", 2018 7th IEEE International Conference on Biomedical Robotics and Biomechatronics (Biorob), pp. 1-6, Aug. 2018.

Tian Tan, et al., "IMU and Smartphone Camera Fusion for Knee Adduction and Knee Flexion Moment Estimation During Walking", IEEE Transactions on Industrial Informatics, vol. 19, No. 2, pp. 1-11, Feb. 2023.

* cited by examiner

TRAINING SYSTEMS AND METHODS FOR PREDICTING KNEE ADDUCTION MOMENT

CROSS-REFERENCE TO RELATED APPLICATIONS

This application is a U.S. National Stage Application filed under 35 U.S.C. § 371(a) claiming the benefit of and priority to International Patent Application No. PCT/US2022/013712, filed Jan. 25, 2022, which claims the benefit of U.S. Provisional Application Ser. No. 63/141,429 filed on Jan. 25, 2021, U.S. Provisional Application Ser. No. 63/166,223 filed on Mar. 25, 2021, and U.S. Provisional Application Ser. No. 63/267,097 filed on Jan. 24, 2022, all of which hereby are incorporated herein by reference, each in their respective entirety.

FIELD

This disclosure generally relates to training systems and methods for early detection of knee osteoarthritis and, in particular, to systems and methods for training a neural network algorithm for predicting early detection of a knee osteoarthritis risk.

BACKGROUND

Osteoarthritis (OA) is a widespread complex chronic disease capable of significantly reducing one's quality of life. As the most common degenerative joint disease, OA causes disability and pain to a large proportion of older adults. In particular, knee OA (KOA) is present in more than 44% of adults aged 80 years old or older and 27% of adults aged 65-69, and there are many factors such as obesity, female gender, and injury to the joint that contribute to this prevalence of KOA. Obesity tends to present itself as the most common risk factor, so as obesity rates increase, it is logical to assume that this widespread disease will only become more prevalent over time.

KOA is characterized by loss of articular and meniscus cartilage, osteophyte formation, bone sclerosis and bone cysts, pathological bone contour alterations, joint malalignment, and other small joint abnormalities. These changes can be detected using radiography and MRI and lead to diagnosis of KOA. Since the alterations to the joint may not be accompanied by pain, asymptomatic KOA could be present for years well before being diagnosed by typical methods. Therefore, methods that can predict early stages of KOA are needed as early-stage KOA is difficult to identify and diagnose.

SUMMARY

This disclosure generally relates to training systems and methods for training artificial neural networks (ANNs), which predict knee adduction moment (KAM) so that the early stage(s) of KOA can be identified.

According to various aspects of the present disclosure, a method for training an algorithm for predicting a knee adduction moment (KAM) includes collecting reference data, as well as training test data. The method includes placing a portable force measurement device under a foot of each of n number of subjects and a motion capturing device over a limb of each of the subjects. While each of the subjects walks on forceplates, the method further includes capturing, by the motion capturing device, kinematic data, generating, by the forceplates, first ground reaction force (GRF) measurement data with a first resolution, generating, by the portable force measurement device, second GRF measurement data with a second resolution lower than the first resolution, and generating reference KAM data based on the kinematic data and the first GRF measurement data.

While repeatedly training the algorithm by incrementing i by one from 1 to n, the method further performs the following steps, which includes generating a model, which predicts KAM data of the subjects based on the second GRF measurement data of the subjects, validating the predicted KAM data of the subjects other than the i-th subject based on the reference KAM data of the subjects other than the i-th subject, adjusting internal parameters of the model by minimizing an error between the predicted KAM data of the subjects other than the i-th subject and the reference KAM data of the subjects other than the i-th subject, and producing an accuracy score for the model based on an error between the predicted KAM data of the i-th subject and the reference KAM data of the i-th subject.

In various aspects, the KAM is represented by a curve. The KAM includes a first peak a second peak, and an average of the curve.

In various aspects, the first peak is greater than the second peak. The first peak and the second peak are local maximums of the curve.

In various aspects, the error is calculated by comparing the first peak, the second peak, and the average of the predicted KAM data, and the first peak, the second peak, and the average of the reference KAM data of the subjects other than the i-th subject, respectively.

In various aspects, validating the predicted KAM data based on reference KAM data includes optimizing the algorithm based on an error between the predicted reference KAM data and the reference KAM data of the subjects other than the i-th subject.

In various aspects, the method further includes normalizing the reference KAM data and the predicted KAM data based on a weight and a height.

In various aspects, the algorithm is a feed-forward neural network, recurrent neural network, or convolutional neural network algorithm.

According to various aspects of the present disclosure, a training system for training an algorithm for predicting a knee adduction moment (KAM) includes a motion capture device configured to be worn over a limb of each of n number of subjects and to capture kinematic data of the subjects, forceplates configured to be stepped on by the subjects and to generate first ground reaction force (GRF) measurement data with a first resolution, a portable force measurement device configured to be worn under a foot of each subject to generate second GRF measurement data with a second resolution lower than the first resolution, a memory storing an algorithm, and a processor configured to generate reference KAM data based on the kinematic data and the first GRF measurement data.

The processor is further configured to repeatedly train the algorithm by incrementing i by one from 1 to n while performing the following steps, which include generating a model, which predicts KAM data of the subjects, validating the predicted KAM data of the subjects other than the i-th subject based on the reference KAM data of the subjects other than the i-th subject, adjusting internal parameters of the model by minimizing an error between the predicted KAM data of the subjects other than the i-th subject and reference KAM data of the subjects other than the i-th subject, and producing an accuracy score for the model based on an error between the predicted KAM data of the i-th subject and the reference KAM data of the i-th subject.

In various aspects, the KAM is represented by a curve. The KAM includes a first peak, a second peak, and an average of the curve In various aspects, the first peak is greater than the second peak. The first peak and the second peak are local maximums of the curve.

In various aspects, validating the predicted KAM data based on reference KAM data includes optimizing the algorithm based on an error between the predicted KAM data and the reference KAM data of the subjects other than the i-th subject.

In various aspects, validating the predicted reference KAM data based on reference KAM data includes optimizing the algorithm based on an error between the predicted KAM data and the reference KAM data.

In various aspects, the processor is further configured to normalize the reference KAM data and the training KAM data based on a weight and a height.

In various aspects, the algorithm is a feed-forward neural network, recurrent neural network, or convolutional neural network algorithm.

In various aspects, the portable force measurement device is an insole device including a plurality of piezo-resistive force sensors.

In various aspects, reflective makers of the motion capture device are placed over the limb of the subjects.

According to various aspects of the present disclosure, a non-transitory computer-readable storage medium includes instructions thereon that, when executed by a computer, cause the computer to perform a method for training an algorithm for predicting a knee adduction moment (KAM). The method includes placing a portable force measurement device under a foot of each of n number of subjects and a motion capturing device over a limb of each of the subjects.

While each of the subjects walks on forceplates, the method further includes capturing, by the motion capturing device, kinematic data, generating, by the forceplates, first ground reaction force (GRF) measurement data with a first resolution, generating, by the portable force measurement device, second GRF measurement data with a second resolution lower than the first resolution, generating reference KAM data based on the kinematic data and the first GRF measurement data, and generating training KAM data based on the second GRF measurement data.

The method further includes repeatedly training the algorithm by incrementing i by one from 1 to n while performing the following steps: generating a model, which predicts KAM data of the subjects, validating the predicted KAM data of the subjects other than the i-th subject based on the reference KAM data of the subjects other than the i-th subject, adjusting internal parameters of the model by minimizing an error between the predicted KAM data of the subjects other than the i-th subject and reference KAM data of the subjects other than the i-th subject, and producing an accuracy score for the model based on an error between the predicted KAM data of the i-th subject and the reference KAM data of the i-th subject.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Various aspects are illustrated in the accompanying figures with the intent that these examples are not restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

FIGS. 4A-6C are graphical representations of real KAM data and prediction data based on an ANN according to various aspects of the present disclosure;

DETAILED DESCRIPTION

Detecting early-stage knee osteoarthritis is difficult, as there are typically no obvious indicators of the disease until pain is present. Predicting a biomechanical risk factor of knee osteoarthritis, knee adduction moment, outside of a laboratory enables data collection of knee loading magnitude and frequency, which affects the damage accumulation of the knee cartilage. Knee adduction moment prediction can lead to detection of knee osteoarthritis before severe progression.

The present disclosure relates generally to systems and methods for training an artificial neural network algorithm for predicting a knee adduction moment. The systems and methods utilize a knee adduction moment measurement system with a portable force measurement device to train a neural network algorithm. The portable force measurement device estimates real-time, resultant ground reaction force by force sensors at points inside of a shoe, where a foot exerts maximal pressure, and estimates three-dimensional ground reaction force magnitude and direction.

The knee adduction moment measurement system generally produces ground reaction force measurement data, which has a higher resolution than that of ground reaction force measurement data of the portable force measurement device. The systems and methods utilize the higher resolution ground reaction force measurement data to train the neural network algorithm so that the neural network algorithm is capable of predicting knee osteoarthritis based on the lower resolution ground reaction force measurement data.

In this disclosure, the following abbreviations are used: Osteoarthritis (OA), Knee Osteoarthritis (KOA), Knee Adduction Moment (KAM), Ground Reaction Force (GRF), Artificial Neural Network algorithm (ANN), Force Sensitive Resistors (FSR), Feed-Forward Neural Network (FFNN), and Analog-to-Digital Converter (ADC).

Figure 1:
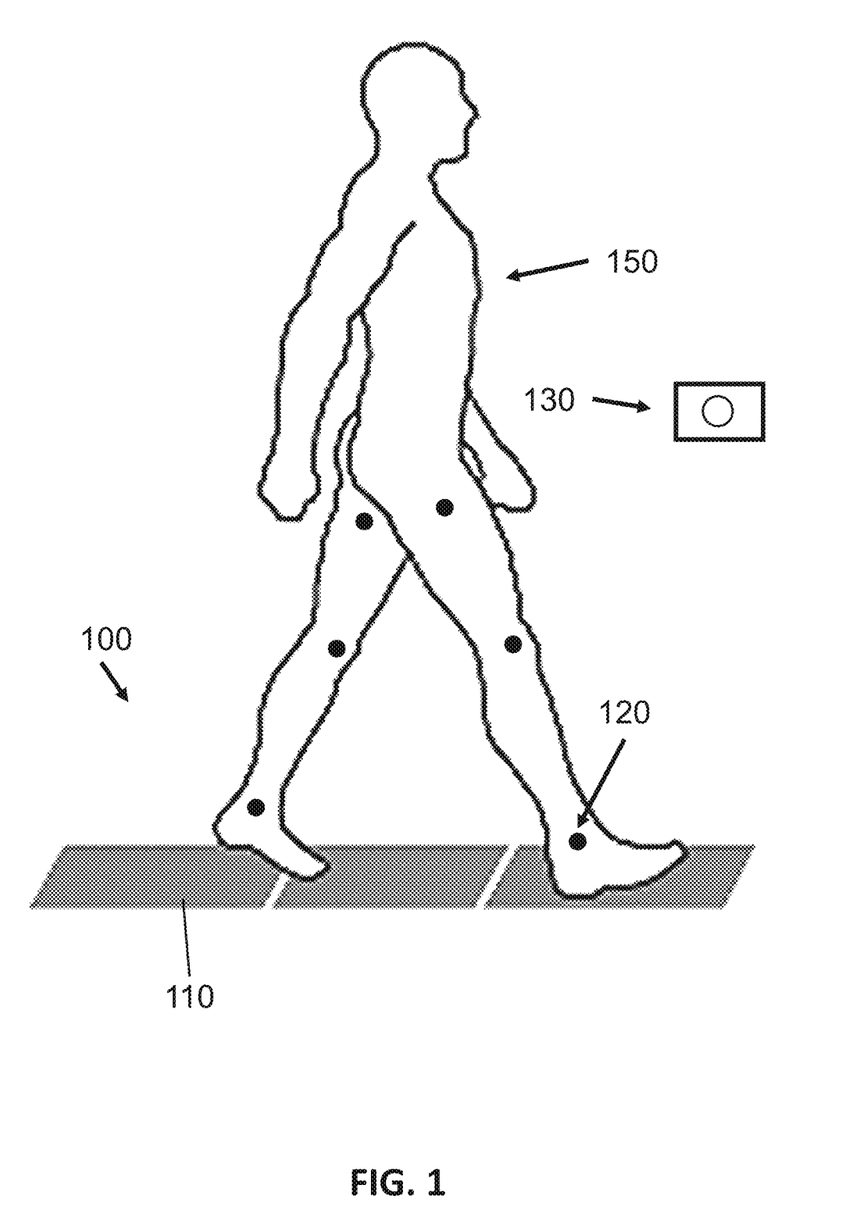
FIG. 1 is a graphical diagram of a conventional knee adduction moment (KAM) measurement system.

Now referring to FIG. 1, illustrated is a conventional KAM measurement system 100 according to various aspects of the present disclosure. The conventional KAM measurement system 100 includes forceplates 110, reflective markers 120, and an image capturing device 130. The forceplates 110 may include one or more force platforms so that a subject 150 can walk one or more steps or even run thereon. Generally, the forceplates 110 are expensive, heavy, and difficult to move, thereby restricting GRF measurement data collection to a small area in a lab. Nevertheless, the forceplates 110 produce GRF measurement data with substantially high accuracy.

Each force platform may measure pressure in 3 directions, for example, namely, X-, Y-, and Z-directions. Along the X-direction, a force along the medial-lateral direction or a direction perpendicular to a walking or running direction is measured, along the Y-direction, a shear force is measured along the anterior-posterior direction or the walking or running direction, and along the Z-direction, a force along the superior-inferior direction or a direction normal to the ground is measured.

The reflective markers 120 may be placed on specific anatomical landmarks of the subject 150 to record virtual coordinates of these anatomical landmarks. The specific anatomical landmarks may be pelvis, thigh, and shank, which are joints of the subject 150. In an aspect, the reflective markers 120 may be placed on anterior and posterior iliac spines, greater trochanters, thigh, medial and lateral femoral condyles, fibulas and tibias.

The image capturing device 130 may capture a still or moving image while the subject walks on the forceplates 110 with the reflective markers 120 thereon. To differentiate the location of the reflective markers 120, the subject 150 may wear non-reflective, tight-fitting clothes (e.g., spandex shorts and shirts). In an aspect, the image capturing device 130 may be more than one image capturing device so that there is no hidden surface from the image capturing devices 130. By performing image processing on the captured images or moving images, changes in the location of the reflective markers 120 can be identified, and based on the changes in the reflective markers 120, the virtual coordinates of the anatomical landmarks can be identified. In this regard, the combination of the reflective markers 120 and the image capturing device 130 may form a motion capture system of the subject 150.

Figure 2:
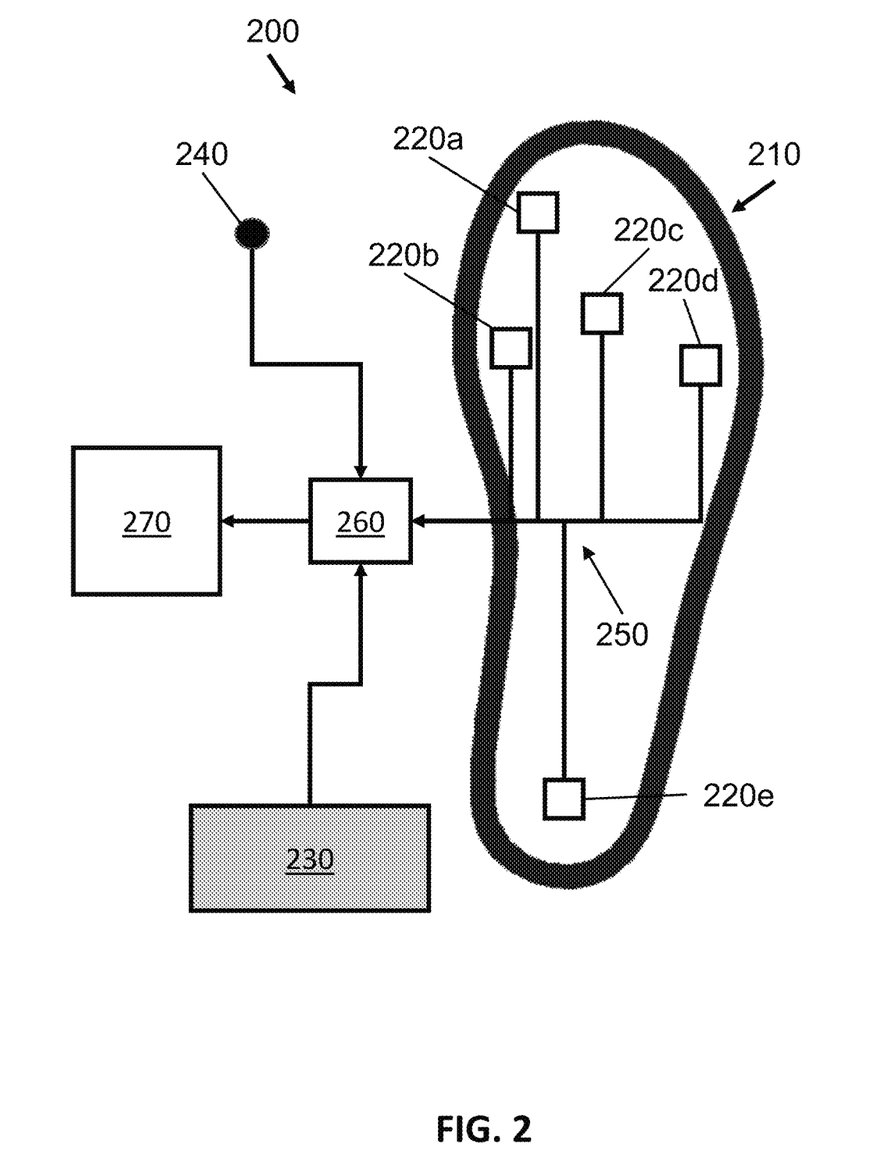
FIG. 2 is a graphical block diagram of a system for training an artificial neural network algorithm (ANN) for predicting a knee adduction moment according to various aspects of the present disclosure.

FIG. 2 shows a training system 200 according to various aspects of the present disclosure. The training system 200 may include a portable measurement device or insole sensor 210, forceplates 230, a motion capture system 240, a communication bus 250, an analog-to-digital converter (ADC) 260, and a computing device 270. The portable measurement device 210 may be installed in a shoe, so that portable measurement device 210 may be wearable by a subject, thereby making measurements possible at any place besides a laboratory environment. On the other hand, the forceplates 230 and the motion capture system 240 may be restricted to a small area in a lab.

The portable measurement device 210 may include force sensors 220a-220e configured to measure forces, in particular GRF, exerted thereon. The placement of the force sensors 210a-210e in the portable measurement device 210 may be designed to minimize disturbances from the subject's movements by positioning the force sensors 210a-210e to contact the sole of the subject's foot. The portable measurement device 210 of FIG. 2 is illustrated for the subject's right foot, but may be made for the subject's left foot in a similar way.

To identify appropriate positions for the force sensors 210a-210e, a stain pad together with a blank pad may be worn by the subject's foot. The stain pad may be a carbon paper. The stain pad may be stapled at the edges thereof with the blank pad. When the subject makes a stance or movements on the pads, the stain is transferred to or trapped in the blank pad as in a form of footprint at places where the foot presses the most on the stain pad. In an aspect, these locations may be the first distal phalanx, first metatarsal joint, third metatarsal joint, fifth metatarsal joint, and calcaneus.

The force sensors 210a-210e may be accordingly affixed on the first distal phalanx, first metatarsal joint, third metatarsal joint, fifth metatarsal joint, and calcaneus of the subject's foot, respectively. The number of the force sensors 210a-210e is not limited to five but may be less than five. For example, the number of the force sensors 210a-210e may be three or two. For example, the force sensors 210a-210e may be placed on the first distal phalanx, the calcaneus, and one of the first metatarsal, third metatarsal, and fifth metatarsal joints, or on the first distal phalanx and the calcaneus.

The portable measurement device 210 may include one or more layers (e.g., top and bottom pads) so that the force sensors 210a-210e may be securely affixed between the top and bottom pads. In an aspect, the top pad may be made of a non-slippery material or include a non-slippery top surface such that the subject's foot may not freely move on the top pad and the force sensors 210a-210e may measure forces at the locations corresponding to the footprint obtained from the stain and blank pads.

To prevent movements of the bottom insole pad 210b, the training system 200 is installed in a shoe, and another pad, which is non-slippery, may be attached to the bottom of the bottom insole pad. Further, to prevent movements of the force sensors 210a-210e between the top and bottom insole pads, another preventive measure may be inserted around the force sensors 210a-210e and between the top and bottom insole pads. The preventive measure may be a mesh sticker or adhesive.

The force sensors 210a-210e may measure GRF exerted thereon and analog GRF measurement data is transferred to the ADC 260 via the communication bus 250. The ADC 260 may convert the analog GRF measurement data into digital GRF measurement data and amplify the amplitude of the analog GRF measurement data. The ADC 260 may include an analog front-end, which includes filters to filter out noises from the analog GRF measurement data.

The ADC 260 is also connected to the forceplates 230 and the motion capture system 240 and may digitize the analog GRF measurement data from the forceplates 230 and the analog kinematic data from the motion capture system 240. In an aspect, the number of ADC 260 may correspond to the number of the force sensors 210a-210e, the forceplates 230, and the motion capture system 240. In other words, at least one ADC 260 is dedicated to a corresponding one of the force sensors 210a-210e, the forceplates 230, and the motion capture system 240. In another aspect, each ADC 260 may have a sampling frequency different from each other. For example, the ADC 260, which is dedicated to the force sensors 210a-210e, may sample the analog GRF measurement data at 100 Hz, the ADC 260, which is dedicated to the forceplates 230, may sample the analog GRF measurement data at 1000 Hz, and the ADC 260, which is dedicated to the motion capture system 240, may sample the analog kinematic data at 120 Hz.

The ADC 260 may be connected to the computing device 270 via a wired connection or a wireless connection. The computing device 270 may receive and process the digitized GRF measurement and kinematic data received via a bus wire (e.g., universal serial bus (USB) or a micro USB). In an aspect, the computing device 270 may transmit to an external computing device the measurement and kinematic data via a wireless connection, which may be Bluetooth®, near field communication (NFC), WiFi™, or any other wireless protocol.

In another aspect, the computing device 270 may include a network interface, which is in a wired connection or wirelessly connected to an external computing device, which is not shown, and transmit the GRF measurement data to the external computing device via the network interface, such as Bluetooth®, NFC, WiFi™, or any other communication protocol. The external computing device may control the computing device 270 to perform the functions/tasks of the training system 200. A customized program may be employed to control the computing device 270.

The computing device 270 may perform training of ANNs with the digitized GRF measurement and kinematic data. For convenience, "digitized" or "digital" may be assumed hereinafter and thus omitted from the GRF measurement data and the kinematic data. The computing device 270 processes may up-sample and/or down-sample the GRF measurement data from the portable measurement device 210 and the forceplates 230 so that both GRF measurement data may have the same data length (e.g., 1024 data points) for one full stance. While adjusting the data length, the computing device 270 may use Butterworth $4^{th}$ order, which is a low pass filter with a cutoff frequency of 10, 12, or 20 Hz. Butterworth $4^{th}$ order is provided as an example and any other low pass filter may be used.

Figure 4A:
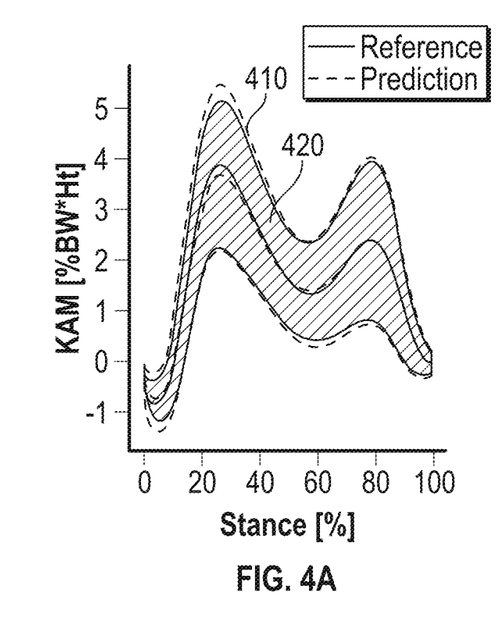

The computing device 270 analyzes the GRF measurement data from the forceplates 230 and the kinematic data from the motion capture system 240, and generates KAM data of the subject, as real or reference KAM data. Briefly referring to FIG. 4A, illustrated are the reference KAM curves 410 and the prediction curve 420. The reference KAM curve 410 is obtained from the KAM data of the subject, as reference KAM data, based on the GRF measurement data from the forceplates 230 and the kinematic data from the motion capture system 240.

The GRF measurement data may differ by subject. For example, sex, age, weight, height, and other physiological features (e.g., body mass index (BMI)) may result in different GRF measurement data. Thus, the KAM data may be normalized based on a weight or a height of the subject. In an aspect, KAM data may be normalized by a product of the weight and the height of the subject.

The horizontal axis of FIG. 4A represents a stance. For example, 0% of the stance may represent when the heel of the foot touches the ground or the forceplates 230 and 100% of the stance may represent when the toes leave the ground or the forceplates 230. The vertical axis may represent KAM, which is normalized by the product of the height and the weight.

The reference KAM curve 410 shows two local maximums, the first peak near 20% of the stance and the second peak near 80% of the stance. An average value and the area under the curve of the reference KAM curve 410 may be calculated. In an aspect, the first peak, the second peak, the average KAM, and the area under the curve of the KAM may be used to predict an early stage of KOA and/or a risk of KOA.

GRF measurement data from the portable measurement device 210 is analyzed by the computing device 270 with the ANN. In other words, the computing device 270 uses the ANN to generate a prediction based on the GRF measurement data from the portable measurement device 210, and the prediction is shown as the prediction curve 420 of FIG. 4A. By comparing the prediction based on the GRF measurement data from the portable measurement device 210 with the reference KAM data based on the forceplates 230 and the motion capture system 240, the computing device 270 computes to adjusts internal parameters of the ANN and report an error therebetween. The error is used to produce an accuracy score for the ANN. In an aspect, portions of the KAM data may be used to adjust the internal parameters of the ANN and the other portion of the KAM data may be used to produce the accuracy score for the ANN.

Figure 3:
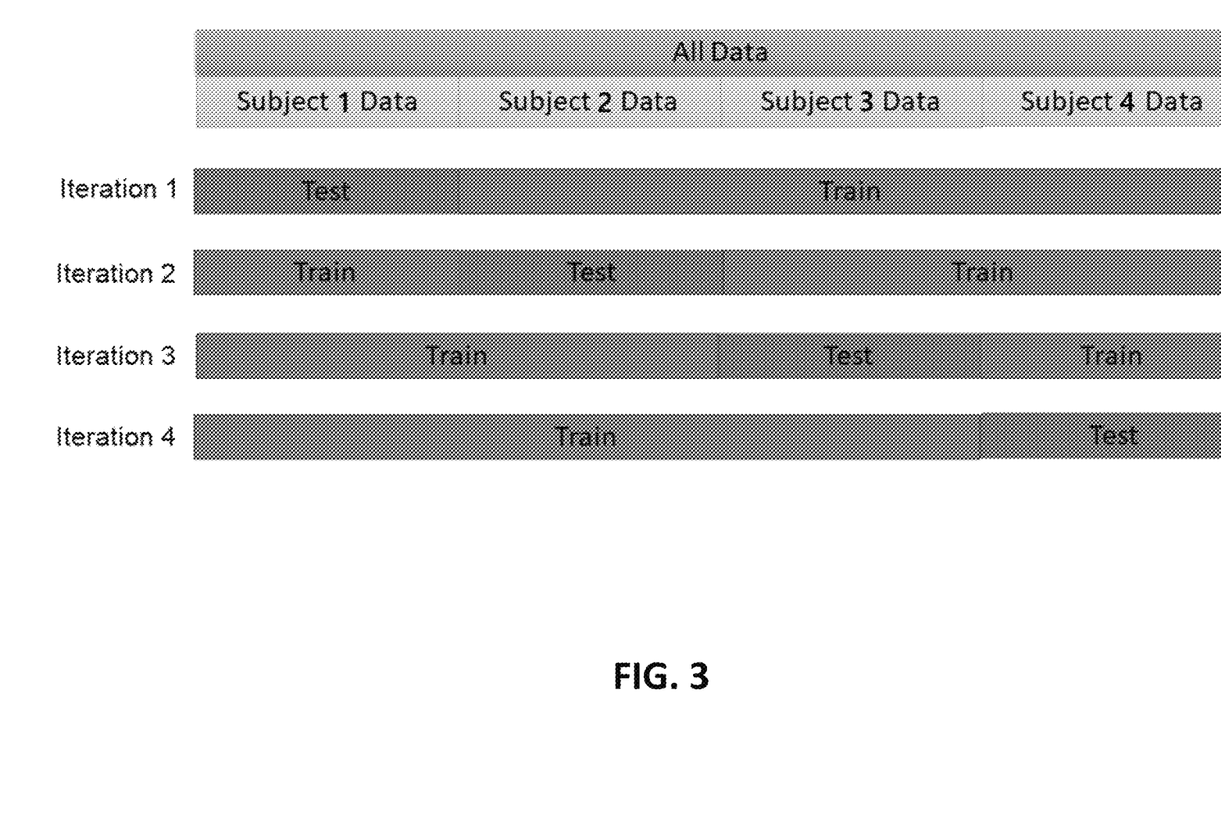
FIG. 3 is a block diagram of cross-validation for training the ANN according to various aspects of the present disclosure.

Now referring to FIG. 3, illustrated is a block diagram showing a cross-validation method in training one or more ANNs according to aspects of the present disclosure. To train one or more ANNs, GRF measurement data from many subjects are needed. The more the number of subjects, the better the training results can be. To train ANNs, the GRF measurement data is separated into two groups, one being a test group and the other being a train group. Generally, data from the train group is used to only adjust internal parameters of the ANN, and data from the test group is used to test how good prediction of the ANN is. On the other hand, FIG. 3 shows how GRF measurement data can be used to both train and test the ANN. For explanation purposes only, FIG. 3 shows GRF measurement data from 4 subjects. Persons having skill in the art reading this disclosure may readily expand this method to any number of subjects.

The GRF measurement data are obtained from the portable measurement device 210 and the forceplates 230, and kinematic data is obtained from the motion capture system 240. To clarify the source of the GRF measurement data, the GRF measurement data from the forceplates 230 is called the first GRF measurement data, and the GRF measurement data from the portable measurement device is called the second GRF measurement data. The computing device 270 may generate reference KAM data from the first GRF measurement data and the kinematic data from the motion capture system 240. The reference KAM data may be shown as the real or reference KAM curve 410 of FIG. 4A.

At Iteration 1, the reference KAM data and the second GRF measurement data from the first subject is set as test data. The reference KAM data from the second, third, and fourth subjects are used to train the ANN. Specifically, the ANN is trained by inputting the second GRF measurement data of the second subject and outputting the reference KAM data of the second subject, inputting the second GRF measurement data of the third subject and outputting the reference KAM data of the third subject, and inputting the second GRF measurement data of the fourth subject and outputting the reference KAM data of the fourth subject. In this way, the ANN is trained and builds a model, which correlates the reference KAM data and the second GRF measurement data.

When the ANN is trained by the second, third, and fourth subjects, the ANN utilizes the model over the second GRF measurement data of the first subject to predict KAM data of the first subject. The predicted KAM data of the first subject may be considered as prediction data as shown in the prediction curve 420 of FIG. 4A.

The internal parameters of the model may be adjusted or fine-tuned by minimizing an error between the predicted KAM data and the reference KAM data of the second, third, and fourth subjects. The computing device 270 compares the predicted KAM data of the first subject with the reference KAM data of the first subject, and computes an error therebetween. In an aspect, the error may be computed by comparing the first peak, the second peak, and the moment. In another aspect, the error between the predicted KAM data of the first subject and the reference KAM data of the first subject may be used to calculate an accuracy score for the ANN. This is the end of Iteration 1.

At Iteration 2, the reference KAM data and the second GRF measurement data from the second subject is set as test data. The reference KAM data from the first, third, and fourth subjects are used to train the ANN. Specifically, the ANN is trained by inputting the second GRF measurement data of the first subject and outputting the reference KAM data of the first subject, inputting the second GRF measurement data of the third subject and outputting the reference KAM data of the third subject, and inputting the second GRF measurement data of the fourth subject and outputting the reference KAM data of the fourth subject. In this way, the model of the ANN is trained, adjusted, and modified.

When the ANN is trained by the first, third, and fourth subjects, the ANN utilizes the model over the second GRF measurement data of the second subject to predict KAM data of the second subject.

The internal parameters of the model may be adjusted or fine-tuned by minimizing an error between the predicted KAM data and the reference KAM data of the first, third, and fourth subjects. The computing device 270 compares the predicted KAM data of the second subject with the reference KAM data of the second subject and computes an error therebetween. In an aspect, the error between the predicted KAM data of the second subject and the reference KAM data of the second subject may be used to calculate an accuracy score for the ANN. This is the end of Iteration 2.

At Iteration 3, the reference KAM data and the second GRF measurement data from the third subject is set as test data. The reference KAM data from the first, second, and fourth subjects are used to train the ANN. At Iteration 4, the reference KAM data and the second GRF measurement data from the fourth subject is set as test data. The reference KAM data from the first, second, and third subjects are used to train the ANN. Iterations 3 and 4 are performed similarly as at Iterations 1 and 2. In this way, one group of GRF measurement data is iteratively used to train and test the ANN by the number of subjects.

In an aspect, the ANN may be a FFNN, RNN, or CNN. The CNN may be used as the primary model, as it is the neural network algorithm that most accurately predicts KAM. This list of the ANNs is not exhaustive but can include other neural network algorithms as readily appreciated by persons skilled in the art.

Figure 6A:
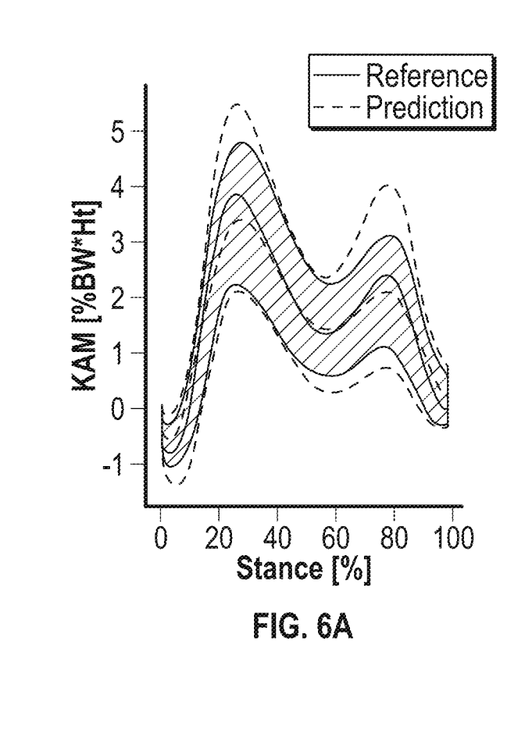
Figure 6B:
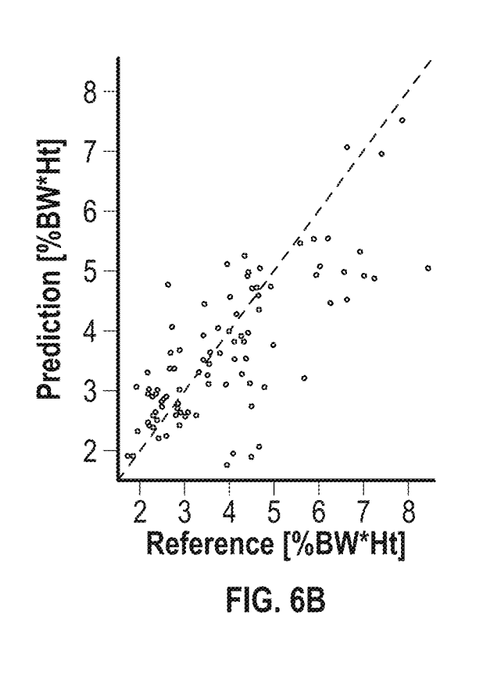
Figure 6C:
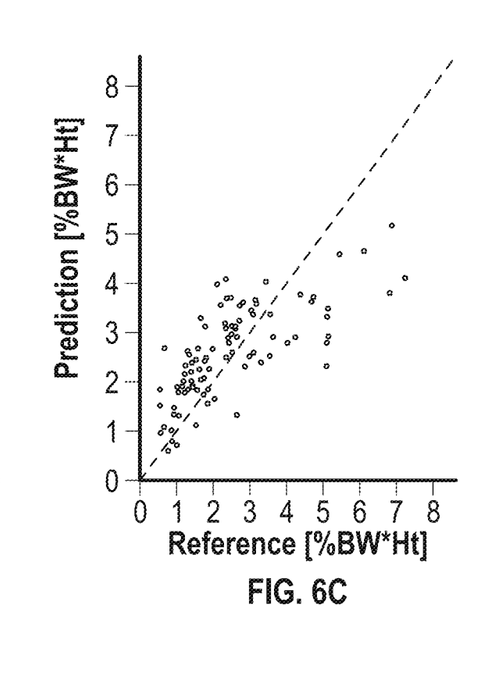

Now referring to FIGS. 4A-6C, illustrated are comparison results between the reference KAM data and predictions obtained by three ANNs according to aspects of the present disclosure. In particular, FIGS. 4A-4C are based on CNN, FIGS. 5A-5C are based on a RNN and FIGS. 6A-6C are based on a FFNN. Again, these three ANNs are provided for explaining purposes only and other ANNs may be used to predict the KAM data from the GRF measurement data from the portable measurement device (e.g., 210 of FIG. 2).

As described above with respect to FIG. 4A, the reference KAM curve 410 is generated as the real or reference KAM data based on the first GRF measurement data from the forceplates (e.g., 230 of FIG. 2) and the kinematic data from the motion capture system (e.g., 240 of FIG. 2). Specifically, the reference KAM curve 410 represents a mean of the first KAM data of the test group. The prediction curve 420 is based on the second GRF measurement data by applying CNN. The prediction curve 420 represents a mean of the test group. Thin gray area 425 represents all data points from the prediction data, and thick grey area 415 represents all data points from the reference KAM data.

Figure 4B:
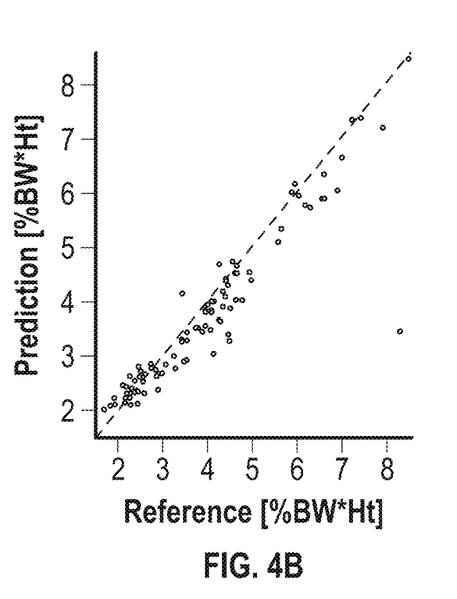
Figure 4C:
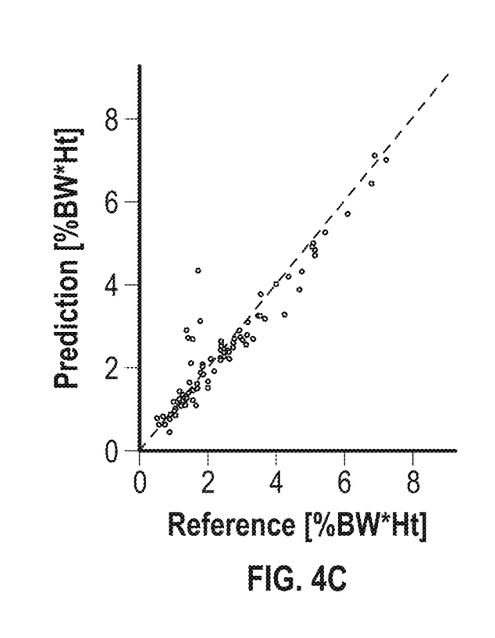
Figure 5A:
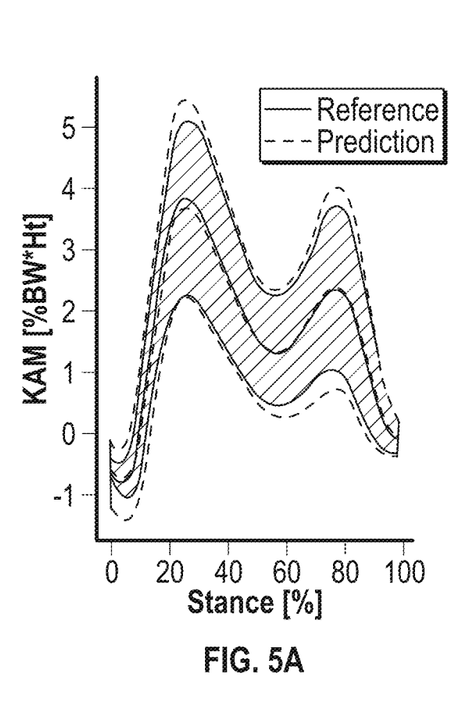
Figure 5B:
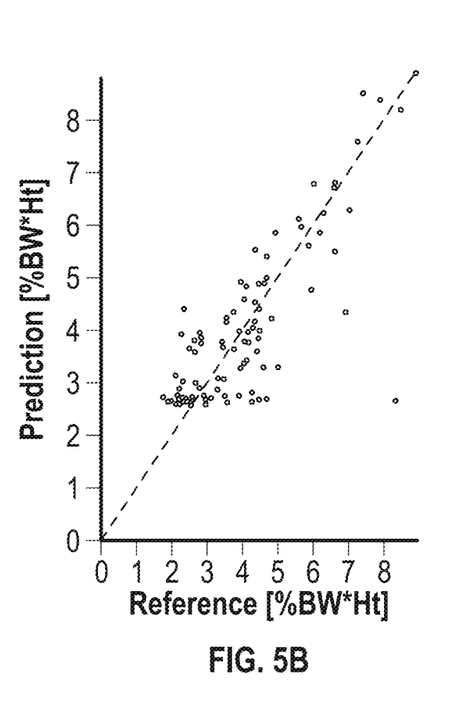
Figure 5C:
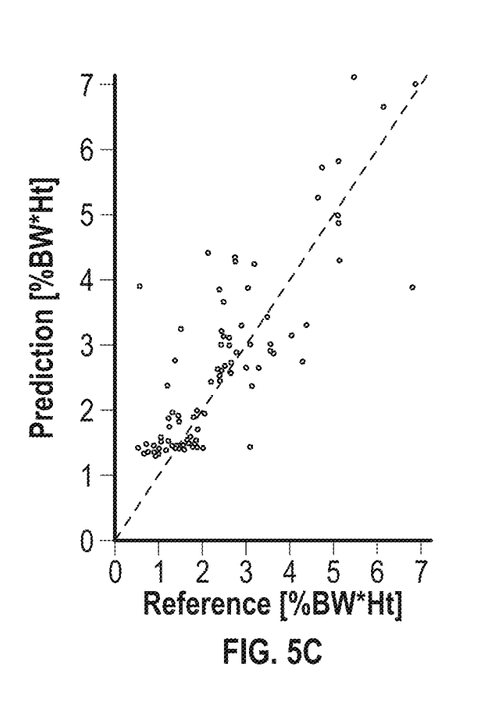

FIG. 4B shows an ideal linear regression line 430 for the first peak and data points of the first peak in the thin gray area 425 of FIG. 4A. The horizontal axis represents reference, which is normalized by the product of the weight and the height of the subjects, and the vertical axis represents the prediction, which is also normalized by the product of the weight and the height of the subjects. FIG. 4C shows an ideal linear regression line 440 for the second peak and data points of the second peak in the thin gray area 425 of FIG. 4A. The horizontal axis represents reference, which is normalized by the product of the weight and the height of the subjects, and the vertical axis represents the prediction, which is also normalized by the product of the weight and the height of the subjects.

The like numerals in the last two digits in FIGS. 5A-6C designate corresponding elements in FIGS. 4A-4C and thus descriptions for the like numerals in FIGS. 5A-6C can be found above in FIGS. 4A-4C.

In consideration of the reference KAM data and the predictions shown in FIGS. 4A-6C, the following Table 1 is made. The first column shows types of ANNs, the second column shows Pearson's correlation coefficient, R, with the 95% confidence interval, and the third column shows the root mean square error (RMSE), which is normalized by the product of weight and height. The first five rows show the total KAM, meaning an average of the KAM, the next five rows show the first peak, and the last five rows show the second peak. As shown in Table 1, CNN performs the best with the highest accuracy and the least errors in all last two columns among FFNN, RNN, and CNN.

TABLE 1

| Model Type | R | RMSE [% BW * Ht] |
|---|---|---|
| | Total KAM | |
| FFNN | 0.84 [0.77; 0.89] | 0.97 |
| RNN | 0.91 [0.87; 0.94] | 0.75 |
| CNN | 0.96 [0.94; 0.97] | 0.47 |
| | Peak 1 | |
| FFNN | 0.73 [0.62; 0.81] | 1.18 |
| RNN | 0.81 [0.73; 0.87] | 0.98 |
| CNN | 0.94 [0.91; 0.96] | 0.63 |
| | Peak 2 | |
| FFNN | 0.72 [0.61; 0.80] | 1.18 |
| RNN | 0.83 [0.76; 0.88] | 0.98 |
| CNN | 0.96 [0.93; 0.97] | 0.63 |

Percent differences between the real KAM data and the predictions are shown in Table 2 according to the ANNs. Specifically, the difference between the first peaks of the real KAM data and the predictions is in the second column, and the difference between the second peaks of the real KAM data and the predictions is in the third column. Based on the differences, CNN also shows the best performance with the least percent difference.

TABLE 2

| Model Type | Peak 1 % | Peak 2 % |
|---|---|---|
| FFNN | 19.75 | 41.40 |
| RNN | 18.89 | 34.65 |
| CNN | 8.18 | 22.01 |

The list of the ANNs of Tables 1 and 2 is provided for explanation purposes only and can include other types of ANNs. Further, the accuracy performance may be different when used with other types of ANNs and different sets of subjects. Nevertheless, the training method can be applied to other types of ANNs to predict reference KAM data from the GRF measurement data from the portable measurement device.

Figure 7:
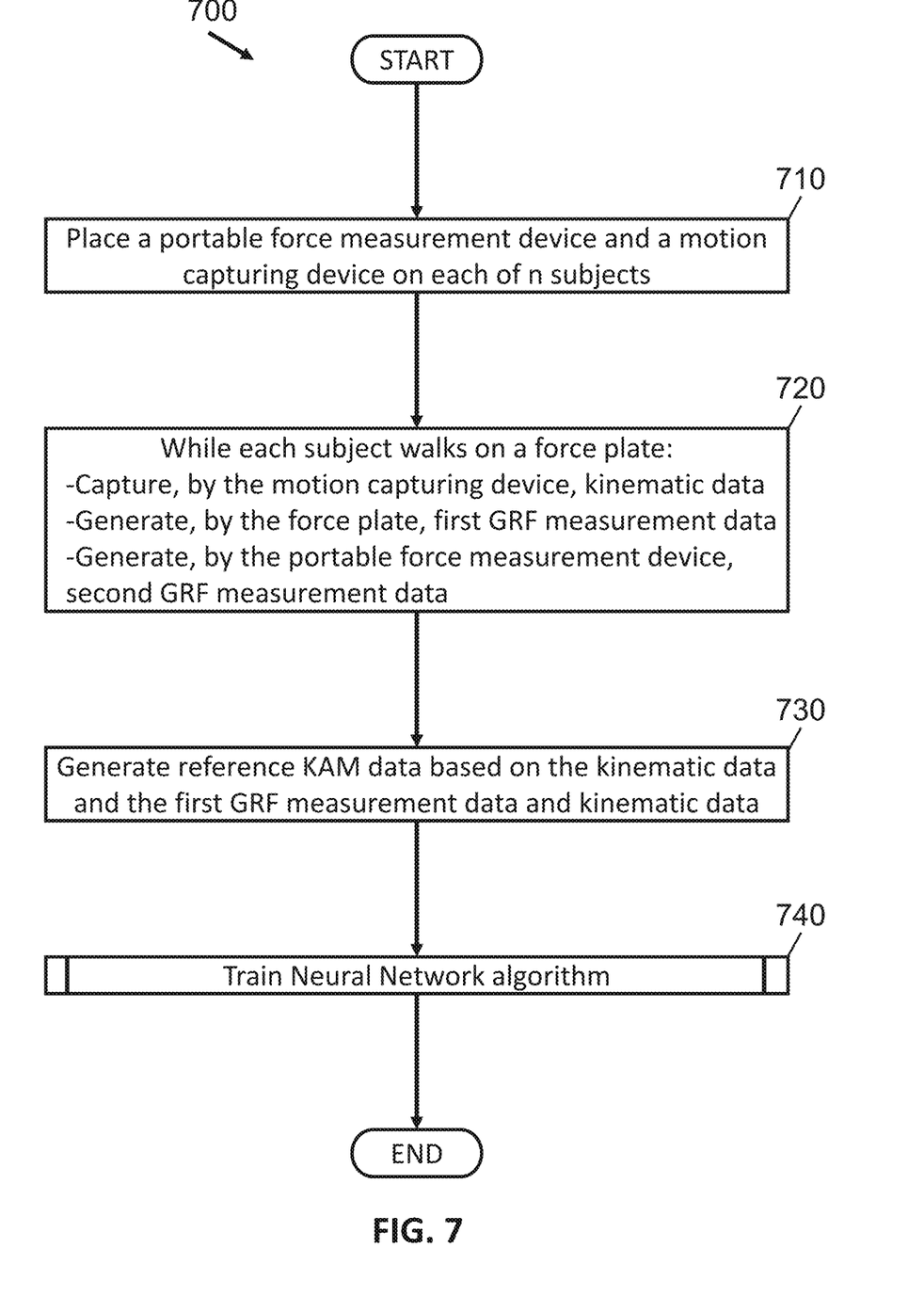
FIG. 7 is a flowchart of a training method for training an ANN for predicting KAM data according to various aspects of the present disclosure.

FIG. 7 shows a flowchart illustrating a training method 700 for training an ANN for predicting KAM according to various aspects of the present disclosure. The training method 700 uses GRF measurement data from n number of subjects to train the ANN so that the ANN produces a prediction based on GRF measurement data from the portable measurement device. The training method 700 is initiated by placing a portable force measurement device (e.g., the insole sensor 210 of FIG. 2) and a motion capture system (e.g., the reflective markers 120 and the image capturing device 130 of FIG. 1) on each of n number of subjects in step 710.

While each of the n subjects walks on a forceplates (e.g., the forceplates 110 of FIG. 1), kinematic data is captured by the motion capture system, first GRF measurement data is generated by the forceplates, and second GRF measurement data is generated by the portable measurement device in step 720. The first GRF measurement data may be sampled at 1000 Hz and the second GRF measurement data may be sampled at 100 Hz. Thus, the resolution of the first GRF measurement data is higher than the resolution of the second GRF measurement data.

By combining the kinematic data and the first GRF measurement data, reference KAM data is generated in step 730. The reference KAM data (e.g., the real or reference KAM curves 410, 510, and 610 of FIGS. 4A, 5A, and 6A, respectively) is real or ideal KAM data from the n subjects. The reference KAM data may be represented as a curve, which shows a first peak and a second peak, which are local maximums of the curve. The first peak is higher than the second peak. In an aspect, the first KAM data may be normalized based on a weight and/or a height. In another aspect, the first KAM data may be normalized based on the product of the weight and the height.

Figure 8:
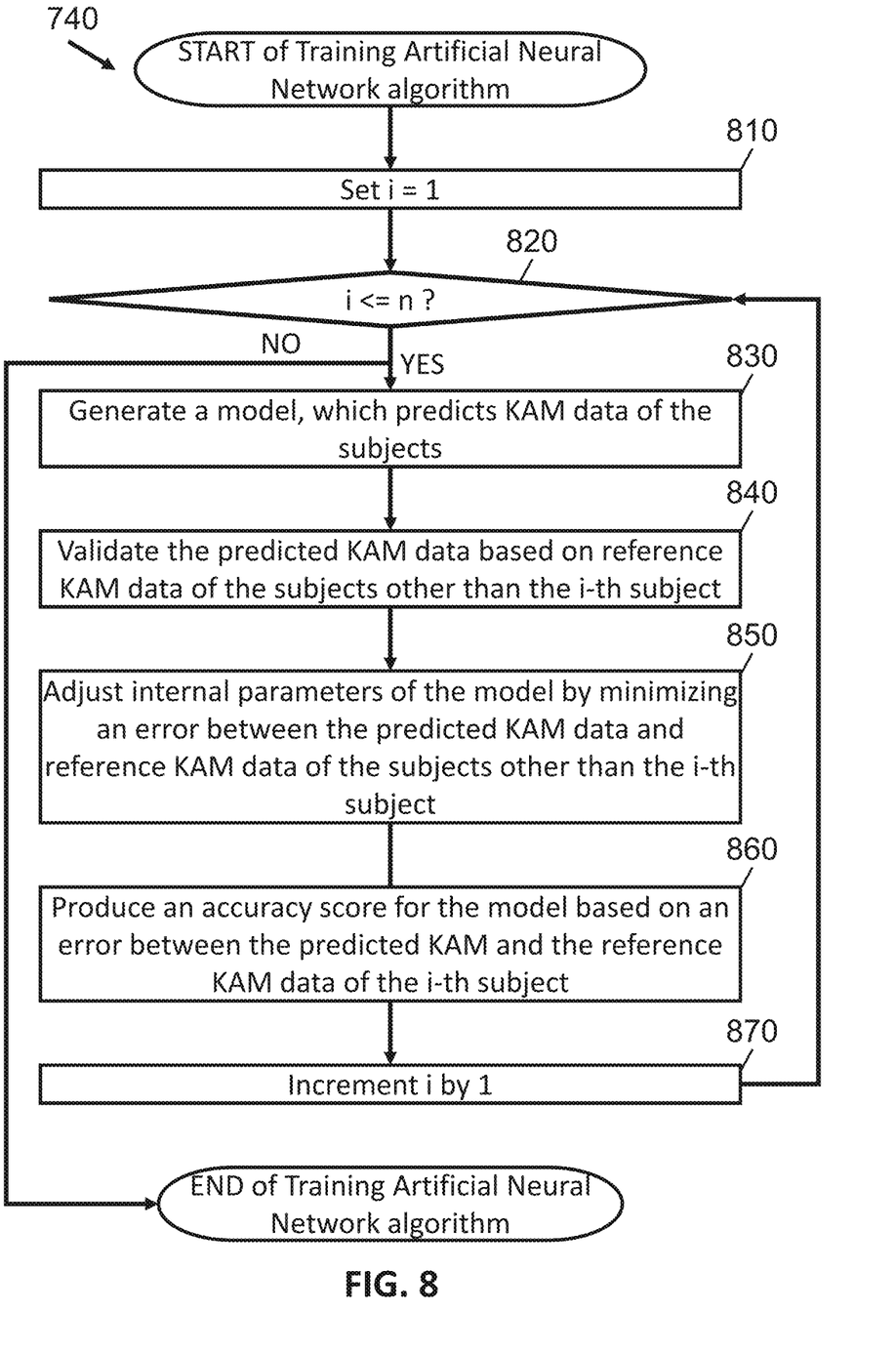
FIG. 8 is a flowchart of a training method for training an ANN for predicting KAM data according to various aspects of the present disclosure.

In step 740, the ANN is trained repeatedly with the second GRF measurement data from the portable measurement device and the reference KAM data. Sub-steps of step 740 are shown in FIG. 8. The training is started by setting an index, as one in step 810. The index i is then compared with the number of subjects, n, in step 820. When it is determined that the index i is greater than the number of subjects, the training is ended and the training method 800 is likewise ended.

When it is determined that the index i is less than or equal to the number of subjects, a model of the ANN is generated in step 830. The model is to predict KAM data of the subjects based on the second GRF measurement data of the subjects. In particular, the model is generated by inputting the second GRF measurement data as an input to the ANN, and outputting the reference KAM data of all the subjects other than the i-th subject, respectively. For example, the second GRF measurement data of (i+1)-th subject is input to the ANN and the ANN generates the reference KAM data of the (i+1)-th subject. By doing this for (n−1) subjects, the ANN is trained, and the model is generated inside the ANN.

In step 840, the predicted KAM data is validated based on the reference KAM data of the subjects other than the i-th subject. In step 850, the internal parameters of the model are adjusted by minimizing the error between the prediction data and the reference KAM data of the subjects not including the i-th subject. By doing this step, the model is fine-tuned.

In step 860, the model is applied to the second GRF measurement data of the i-th subject to predict KAM data as prediction data. The predicted KAM data of the i-th subject is compared with the reference KAM data of the i-th subject. The difference between the reference KAM data and the predicted KAM data of the i-th subject is used to produce an accuracy score for the model.

In step 870, the index, i, is incremented by one and steps 820-870 are repeatedly performed until the index, i, is greater than the number of subjects, n. With this training method 800, GRF measurement data from n subjects can be used n times repeatedly by switching the train group of (n−1) subjects and the test group of one subject.

Figure 9:
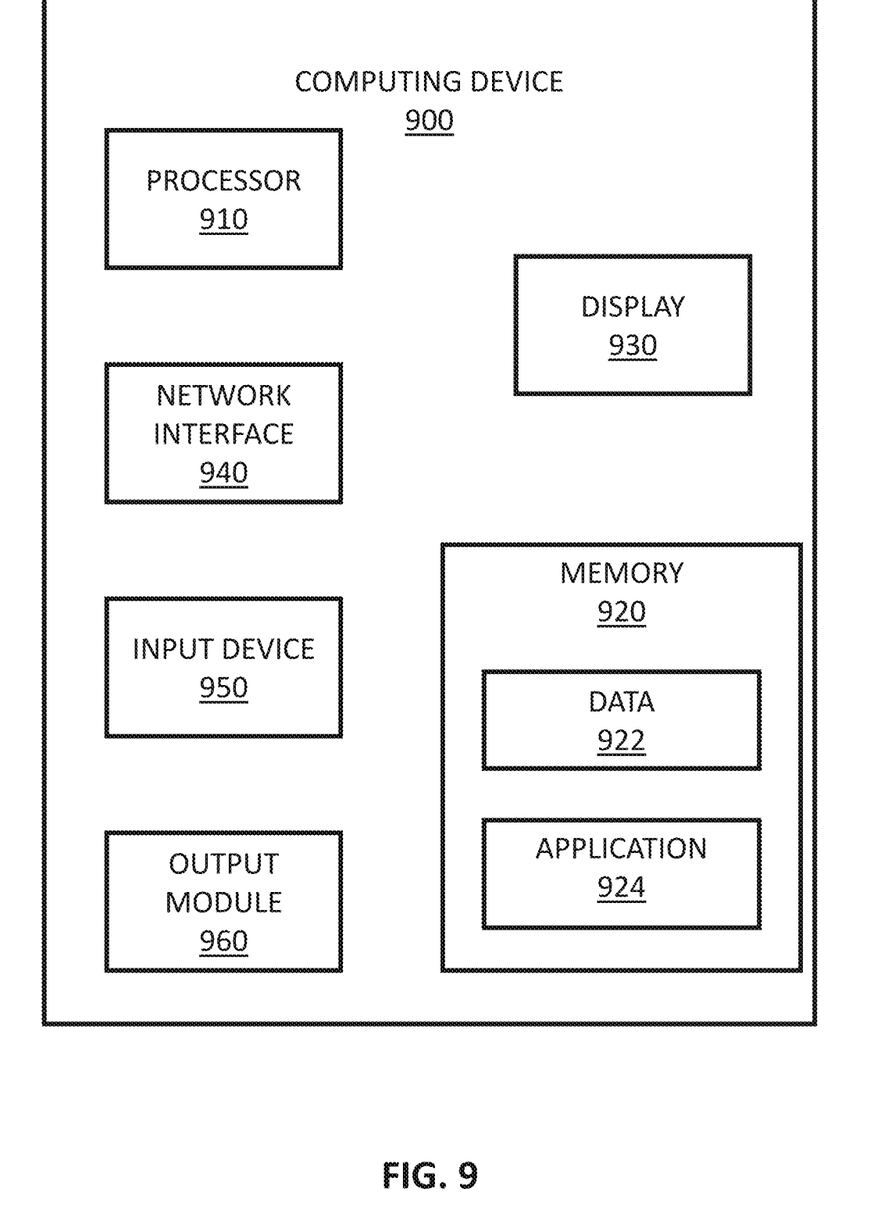
FIG. 9 is a block diagram of a computing device according to various aspects of the present disclosure.

Turning now to FIG. 9, a block diagram is provided for a computing device 900, which can be the computing device 270 of FIG. 2. The computing device 900 may include a processor 910, a memory 920, a display 930, a network interface 940, an input device 950, and/or an output module 960. The memory 920 may include any non-transitory computer-readable storage media for storing data and/or software that is executable by the processor 910 and which controls the operation of the computing device 900.

In an aspect, the memory 920 may include one or more solid-state storage devices such as flash memory chips. Alternatively, or in addition to the one or more solid-state storage devices, the memory 920 may include one or more mass storage devices connected to the processor 910 through a mass storage controller (not shown) and a communications bus (not shown).

Although the description of computer-readable media contained herein refers to a solid-state storage, it should be appreciated by those skilled in the art that computer-readable storage media can be any available media that can be accessed by the processor 910. That is, computer-readable storage media may include non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which can be used to store the desired information, and which can be accessed by the computing device 900.

The memory 920 may store application 924 (e.g., ANNs) and/or data 922 (e.g., the model of the ANN, the GRF measurement data from the forceplates 230 and the force sensors 220a-220e). The application 924 may, when executed by processor 910, perform training ANNs based on the GRF measurement data as described above. In an aspect, the application 924 will be a single software program having all of the features and functionality described in the present disclosure. In another aspect, the application 924 may be two or more distinct software programs providing various parts of these features and functionality.

Various software programs forming part of the application 924 may be enabled to communicate with each other and/or import and export various settings and parameters relating to adjusting internal parameters of a model of the ANNs for predicting KAM. The application 924 communicates via a user interface to present visual interactive features to the user on the display 930. For example, the graphical illustrations may be outputted to the display 930 to present graphical illustrations as shown in FIGS. 3A-5C.

The application 924 may include a sequence of process-executable instructions, which can perform any of the herein described methods, programs, algorithms or codes, which are converted to, or expressed in, a programming language or computer program. The terms "programming language" and "computer program," as used herein, each includes any language used to specify instructions to a computer, and includes (but is not limited to) the following computer languages and their derivatives: Assembler, BASIC, batch files, BCPL, C, C+, C++, COBOL, Delphi, Fortran, Java, JavaScript®, machine code, intermediate language(s), operating system command languages, Pascal, Perl, PL1, scripting languages, Visual Basic, meta-languages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

The processor 910 may be a general purpose processor, a specialized graphics processing unit (GPU) configured to perform specific graphics processing tasks or parallel processing while freeing up the general purpose processor to perform other tasks, and/or any number or combination of such processors, digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure(s) or any other physical structure(s) suitable for implementation of the described operations. Also, the techniques could be fully implemented in one or more circuits or logic elements.

The display 930 may be touch-sensitive and/or voice-activated, enabling the display 930 to serve as both an input and output device. Alternatively, a keyboard (not shown), mouse (not shown), or other data input devices may be employed. The network interface 940 may be configured to connect to a network such as a local area network (LAN) consisting of a wired network and/or a wireless network, a wide area network (WAN), a wireless mobile network, a Bluetooth network, and/or the internet.

For example, the computing device 900 may receive, through the network interface 940, GRF measurement data from the forceplates 230 and the force sensors 220a-220e of FIG. 2, for example, which is time-series data in a stance, walking, or running mode. The computing device 900 may receive updates to its software, for example, the application 924, via the network interface 940. The computing device 900 may also display notifications on the display 930 that a software update is available.

The input device 950 may be any device by means of which a user may interact with the computing device 900, such as, for example, a mouse, keyboard, voice interface, or the forceplates 230 and the force sensors 220a-220e of FIG. 2. The output module 960 may include any connectivity port or bus, such as, for example, parallel ports, serial ports, universal serial busses (USB), or any other similar connectivity port known to those skilled in the art. In an aspect, the application 924 may be installed directly on the computing device 900 or via the network interface 940. The application 924 may run natively on the computing device 900, as a web-based application in a cloud via the network interface 940, or any other format known to those skilled in the art.

The various aspects disclosed herein are examples of the disclosure and may be embodied in various forms. Although certain embodiments herein are described as separate embodiments, each of the embodiments herein may be combined with one or more of the other embodiments herein. It should also be understood that, depending on the example, certain acts or events of any of the processes or methods described herein may be performed in a different sequence, may be added, merged, or left out altogether (e.g., all described acts or events may not be necessary to carry out the techniques). In addition, Specific structural and functional details disclosed herein are not to be interpreted as limiting, but as a basis for the claims and as a representative basis for teaching one skilled in the art to variously employ the present disclosure in virtually any appropriately detailed structure.

What is claimed is:

1. A method for training an algorithm for predicting a knee adduction moment (KAM), the method comprising:
   placing a portable force measurement device under a foot of each of n number of subjects and a motion capturing device over a limb of each of the subjects;
   while each of the subjects walks on forceplates:
      capturing, by the motion capturing device, kinematic data;
      generating, by the forceplates, first ground reaction force (GRF) measurement data with a first resolution;
      generating, by the portable force measurement device, second GRF measurement data with a second resolution lower than the first resolution; and
      generating reference KAM data based on the kinematic data and the first GRF measurement data; and
   repeatedly training the algorithm by incrementing i by one from 1 to n while performing the following steps:
      generating a model, which predicts KAM data of the subjects based on second GRF measurement data of the subjects;
      validating the predicted KAM data of the subjects other than the i-th subject based on the reference KAM data of the subjects other than the i-th subject;
      adjusting internal parameters of the model by minimizing an error between the predicted KAM data of the subjects other than the i-th subject and the reference KAM data of the subjects other than the i-th subject; and
      producing an accuracy score for the model based on an error between the predicted KAM data of the i-th subject and the reference KAM data of the i-th subject.

2. The method according to claim 1, wherein the KAM is represented by a curve.

3. The method according to claim 2, wherein the KAM includes a first peak, a second peak, and an average of the curve.

4. The method according to claim 3, wherein the first peak is greater than the second peak.

5. The method according to claim 3, wherein the first peak and the second peak are local maximums of the curve.

6. The method according to claim 3, wherein the error is calculated by comparing the first peak, the second peak, and the average of the predicted KAM data, and the first peak, the second peak, and the average of the reference KAM data of the subjects other than the i-th subject, respectively.

7. The method according to claim 3, wherein validating the predicted reference KAM data based on reference KAM data includes optimizing the algorithm based on an error between the predicted reference KAM data and the reference KAM data of the subjects other than the i-th subject.

8. The method according to claim 1, further comprising: normalizing the reference KAM data and the predicted KAM data based on a weight and a height.

9. The method according to claim 1, wherein the algorithm is a feed-forward neural network, recurrent neural network, or convolutional neural network algorithm.

10. A training system for training an algorithm for predicting a knee adduction moment (KAM), the training system comprising:
a motion capture device configured to be worn over a limb of each of n number of subjects and to capture kinematic data of the subjects;
forceplates configured to be stepped on by the subjects and to generate first ground reaction force (GRF) measurement data with a first resolution;
a portable force measurement device configured to be worn under a foot of each subject to generate second GRF measurement data with a second resolution lower than the first resolution;
a memory storing an algorithm; and
a processor configured to:
generate reference KAM data based on the kinematic data and the first GRF measurement data; and
repeatedly train the algorithm by incrementing i by one from 1 to n while performing the following steps:
generating a model, which predicts KAM data of the subjects;
validating the predicted KAM data of the subjects other than the i-th subject based on the reference KAM data of the subjects other than the i-th subject;
adjusting internal parameters of the model by minimizing an error between the predicted KAM data of the subjects other than the i-th subject and reference KAM data of the subjects other than the i-th subject; and
producing an accuracy score for the model based on an error between the predicted KAM data of the i-th subject and the reference KAM data of the i-th subject.

11. The training system according to claim 10, wherein the KAM is represented by a curve.

12. The training system according to claim 11, wherein the KAM includes a first peak, a second peak, and an average of the curve.

13. The training system according to claim 12, wherein the first peak is greater than the second peak.

14. The training system according to claim 12, wherein the first peak and the second peak are local maximums of the curve.

15. The training system according to claim 10, wherein validating the predicted KAM data based on reference KAM data includes optimizing the algorithm based on an error between the predicted KAM data and the reference KAM data of the subjects other than the i-th subject.

16. The training system according to claim 10, wherein the processor is further configured to normalize the reference KAM data and the predicted KAM data based on a weight and a height.

17. The training system according to claim 10, wherein the algorithm is a feed-forward neural network, recurrent neural network, or convolutional neural network algorithm.

18. The training system according to claim 10, wherein the portable force measurement device is an insole device including a plurality of piezo-resistive force sensors.

19. The training system according to claim 10, wherein reflective makers of the motion capture device are placed over the limb of the subjects.

20. A non-transitory computer-readable storage medium including instructions thereon that, when executed by a computer, cause the computer to perform a method for training an algorithm for predicting a knee adduction moment (KAM), the method comprising:
placing a portable force measurement device under a foot of each of n number of subjects and a motion capturing device over a limb of each of the subjects;
while each of the subjects walks on forceplates:
capturing, by the motion capturing device, kinematic data;
generating, by the forceplates, first ground reaction force (GRF) measurement data with a first resolution;
generating, by the portable force measurement device, second GRF measurement data with a second resolution lower than the first resolution;
generating reference KAM data based on the kinematic data and the first GRF measurement data; and
repeatedly training the algorithm by incrementing i by one from 1 to n while performing the following steps:
generating a model, which predicts KAM data of the subjects;
validating the predicted KAM data of the subjects other than the i-th subject based on reference KAM data of the subjects other than the i-th subject;
adjusting internal parameters of the model by minimizing an error between the predicted KAM data of the subjects other than i-th subject and reference KAM data of the subjects other than i-th subject; and
producing an accuracy score for the model based on an error between the predicted KAM data of the i-th subject and the reference KAM data of the i-th subject.

* * * * *